United States Patent [19]

Malick

[11] 4,181,576

[45] Jan. 1, 1980

[54] FERMENTATION METHOD

[75] Inventor: Emil A. Malick, Bartlesville, Okla.

[73] Assignee: Phillips Petroleum Company, Bartlesville, Okla.

[21] Appl. No.: 931,636

[22] Filed: Aug. 7, 1978

Related U.S. Application Data

[62] Division of Ser. No. 782,599, Mar. 29, 1977, Pat. No. 4,148,691.

[51] Int. Cl.² .............................................. C12B 1/00
[52] U.S. Cl. .................................... 435/247; 435/813; 435/313; 435/316
[58] Field of Search ............... 195/109, 105, 115, 142, 195/143, 144, 107

[56] References Cited

U.S. PATENT DOCUMENTS

| | | | |
|---|---|---|---|
| 2,244,902 | 6/1941 | Stich | 195/142 |
| 2,913,343 | 11/1959 | Richardson | 195/143 X |
| 3,460,810 | 8/1969 | Mueller | 195/143 X |
| 3,957,585 | 5/1976 | Malick | 195/109 |
| 3,969,190 | 7/1976 | Hise et al. | 195/109 X |

*Primary Examiner*—Raymond N. Jones
*Assistant Examiner*—Robert J. Warden

[57] ABSTRACT

A fermentation apparatus of the loop flow type includes a tubular member forming a continuous or substantially continuous loop flow path defined by the interior surface of the tubular member. A heat exchanger surrounds a portion of the tubular member and is in heat transfer relation thereto and inside the tubular member at the point where the heat exchange means surrounds the tubular member mixing vanes or fins are secured to the tubular member to effect mixing of medium flowing through the tubular member. A spray nozzle is provided just upstream of the mixing vanes and is operable for discharge of medium into the flow path adjacent the heat exchange means. A pump is connected to the nozzle and pressurizes medium taken from the flow path and discharges same through the nozzle. Injectors open into the flow path adjacent the heat exchange means and are operable for introducing an oxygen-containing gas into the medium contained in the flow path. A phase separator has an inlet and outlet communicating with the flow path and is operable for receiving a portion of the medium for separating same into a gas phase and liquid phase and returning a portion of the liquid phase to the flow path.

7 Claims, 5 Drawing Figures

FERMENTATION METHOD

This application is a division of copending application Ser. No. 782,599, filed Mar. 29, 1977 now U.S. Pat. No. 4,148,691.

Many apparatuses are known in the art for conducting fermentation wherein a microorganism is cultured to produce single cell protein (SCP) wherein the microorganism uses a carbon source such as methanol for growth in which the growth process also requires an assimilable form of oxygen and other nutrients and minerals as is known in the art. Typical of this type of apparatus is a vessel which has therein a draft tube wherein medium flows through the draft tube and then through an annular space between the draft tube and the interior of the vessel. This is a type of loop flow reactor but requires a closed vessel and a tubular member positioned therein with open opposite ends. Another type of typical reactor is that in which a tubular member forms a loop wherein air is sparged into one upstanding leg of the loop wherein the lighter density foam formed rises in the leg and a phase separation occurs at the top after which the densified liquid phase returns through the other upstanding leg and back into the riser leg of the apparatus. Both of these types of apparatus are effective for producing single cell protein by fermentation and the present invention offers an alternate apparatus thereto. One of the problems in producing single cell protein by a fermentation process is supplying an adequate amount of assimilable oxygen to the medium to effect an adequate growth rate of the mioorganism. A foam type process has been found to be effective in accomplishing high rates of oxygen transfer wherein the high surface area contact between the oxygen and the liquid medium helps accomplish the high oxygen transfer rate. This can also be accomplished by the use of a nozzle for atomizing the liquid medium and contacting tiny droplets thereof with oxygen to effect the high surface area contact therebetween. It is also important in fermentation processes to eliminate any stagnant zones, i.e., areas in which the medium does not flow, to accomplish the highest productivity. It is also desirable to remove heat so as to maintain the medium at its optimum growth temperature. Since the fermentation processes known to date are highly exothermic, heat transfer is a major problem. Attempts to overcome the above problems have met with difficulty mainly in the cost of capital equipment in that to provide an apparatus with adequate heat transfer area and adequate mixing means requires a highly complicated structure which is difficult to build and maintain, and, likewise, expensive to operate.

The principal objects and advantages of the present invention are: to provide an apparatus for conducting fermentation which overcomes the above-described difficulties; to provide such an apparatus which is simple in construction and operation; to provide such an apparatus which effects good contact of the medium with an assimilable form of oxygen with a high surface area of contact therebetween; to provide such an apparatus which effects good mixing of the medium flowing through the apparatus; and to provide such an apparatus which is well adapted for its intended use.

Other objects and advantages of the present invention will become apparent from the following detailed description taken in connection with the accompanying drawings wherein are set forth by way of illustration and example certain embodiments of this invention.

Figure 1:
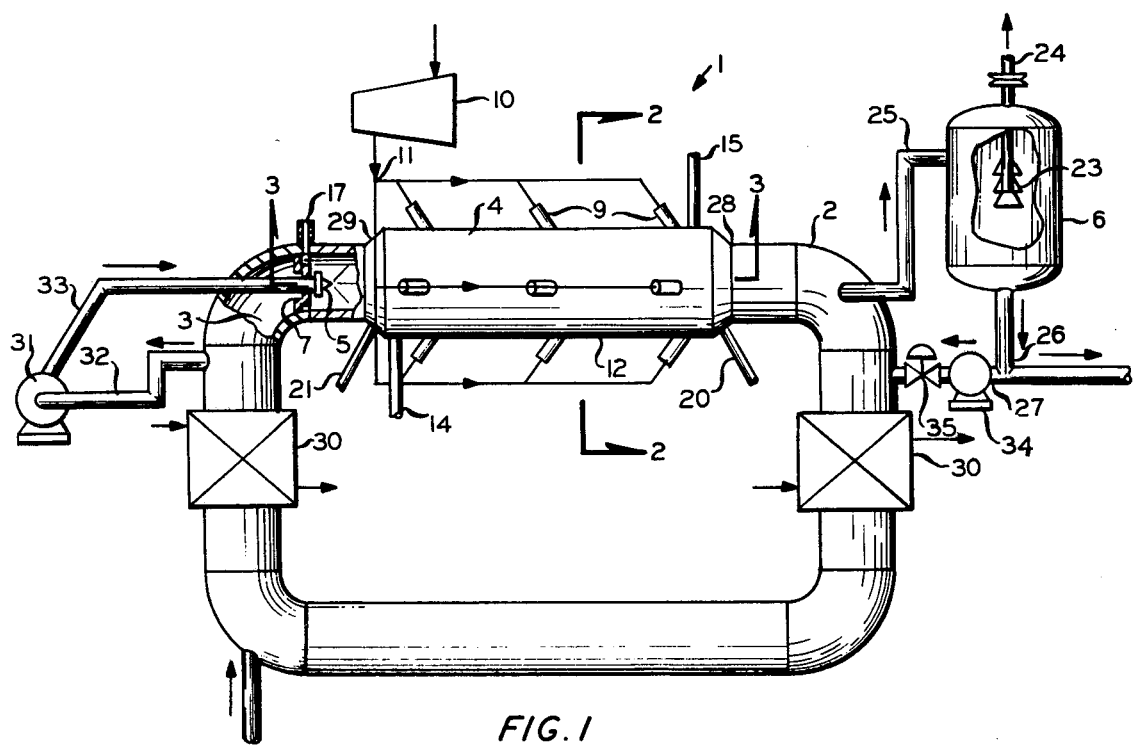
FIG. 1 is a somewhat schematic plan view of a fermentation apparatus.

Referring more in detail to the drawings:

As required, detailed embodiments of the present invention are disclosed herein, however, it is to be understood that the disclosed embodiments are merely exemplary of the invention which may be embodied in various forms. Therefore, specific structural and functional details disclosed herein are not to be interpreted as limiting, but merely as a basis for the claims and as a representative basis for teaching one skilled in the art to variously employ the present invention in virtually any appropriate structure.

The reference numeral 1 designates generally an apparatus for conducting fermentation processes such as those used for the production of single cell protein. The apparatus 1 includes a tubular member 2 which is in the form of a continuous or substantially continuous loop defining a flow path or reaction zone 3 therein. The apparatus 1 also includes means 4 which is operable for inducing fermentation or improved fermentation to occur. A nozzle 5 is also provided and is operable for spraying medium, i.e., the fluid which contains assimilable oxygen, nutrients, carbon source, etc., as is known in the art. Phase separation means 6 communicates with the flow path 3 and is operable for receiving foam from the flow path and separating the foam into a liquid phase and a gas phase wherein a portion of the liquid phase can be returned to the flow path and the gas phase can be exhausted.

The tubular member 2 can be of any suitable type and in operation is endless whereby medium continuously flows through the flow path 3. The tubular member 2 preferably is made of stainless steel and can be of any suitable size as is dictated by the particular requirements for the particular fermentation process being conducted therein. What is meant by continuous or substantially continuous or endless is that one tubular member forms the flow path as opposed to the draft tube in a vessel type of fermenter wherein loop flow is accomplished. However, the tubular member 2 can have one or more partitions 7 therein to prevent flow of fluid from one portion of the flow path into another portion of the flow path except in a manner as described below.

Figure 2:
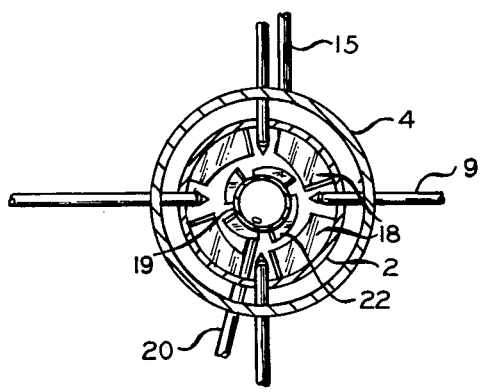
FIG. 2 is a sectional view of the fermentation apparatus taken along the line 2—2, FIG. 1.
Figure 3:
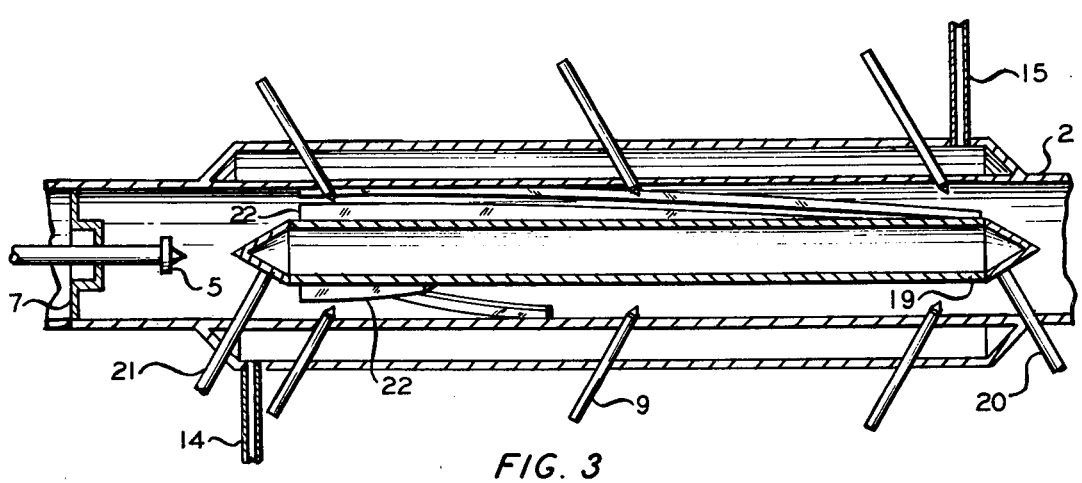
FIG. 3 is a sectional view of the apparatus taken along the line 3—3, FIG. 1.
Figure 5:
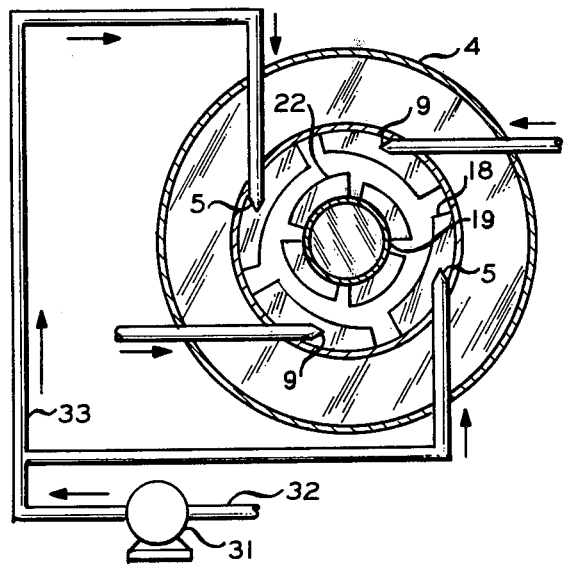
FIG. 5 is a somewhat schematic sectional view of a modified form of the present invention and would also be taken generally along the line 2—2, FIG. 1.

In a preferred form of the invention as seen in FIG. 1, the fermentation inducing means 4 includes a plurality of air injectors 9 which are positioned adjacent to one another and open into the flow path 3 and are connected to a source of assimilable oxygen such as air which is pressurized as, for example, by a compressor 10. The compressor 10 is connected to the injectors 9 by a plurality of conduits 11. The injectors 9 can be directed in any suitable direction and can be directed in a generally tangential manner as seen in FIG. 5 or generally radially as seen in FIG. 2 and can also be canted in a downstream direction. The means 4 also includes heat exchange means 12 positioned adjacent the air injectors 9 and as shown the heat exchange means is a jacket type heat exchanger positioned around the exterior of the tubular member 2 and has the injectors 9 extending through the heat exchanger 12 and the tubular member 2. Coolant is introduced into the heat exchanger 12 via a conduit 14 and is discharged through a discharge conduit 15. As shown, the means 4 is positioned immediately adjacent to and just downstream of the nozzle 5 with the nozzle 5 being directed generally axially down the flow path 3 and is operable for spraying medium into an area within the flow path surrounded by the heat exchange means for contact with air introduced by the injectors 9. The nozzle 5 can be of any suitable construction and preferably is of a type which will finely atomize the medium discharged therethrough. Preferably, the nozzle 5 is mounted on the partition 7. It is to be noted that the partition 7 can have air introduced around the nozzle 5 via an inlet 17.

The means 4 also includes means for effecting mixing of the medium as same flows along the tubular member in the vicinity of at least the heat exchanger 12. As shown, the mixing means includes a plurality of helically disposed mixing vanes 18 which preferably are secured to the interior surface of the tubular member 2 and extend into the flow path and are disposed circumferentially around the tubular member 2. Any suitable number can be provided and the height of the mixing vane and the length of the mixing vane are determined by the particular process and the degree of mixing desired. It is also to be noted that the mixing vanes 18 can be positioned in other portions of the tubular member 2 to help induce mixing of the medium as same flows along the flow path 3. Although not required, a second heat exchanger 19 can be provided and as shown, same is positioned within the tubular member 2 in proximity to the heat exchange means 12. The heat exchanger 19 as shown is an axially extending tubular member which has an inlet 20 for providing coolant from a suitable source to flow along the tubular member to a discharge 21 for discharge of the heated coolant. The heat exchanger 19 as shown is positioned generally centrally within the tubular member 2 and can extend from within the confines of the heat exchanger 12 into other portions of the tubular member 2 as is required by the particular fermentation process. Preferably, the heat exchanger 19 has a plurality of fins 22 extending therefrom to help effect heat transfer with medium flowing thereby and the fins 22 can also be helically disposed to help provide mixing of medium flowing by the heat exchanger 19. Both the heat exchangers 12 and 19 are in heat transfer relation in any suitable manner with the medium flowing through the flow path 3. The tubular member 2 as described above includes the wall defining the flow path 3 within the heat exchange means 12.

The phase separator 6 can be of any suitable type as is known in the art such as that which uses a plurality of truncated cone-shaped members 23 rotated about an axis for centrifugal separation of the foam into gas and liquid. (For clarity, the phase separator 6 is shown in the wrong plane where in actual construction the axis of the shaft would be generally vertical and the discharge 26 would be located in the bottom, i.e., 90° from the position shown). The phase separator has a gas exhaust 24 which communicates with the interior of the phase separator, preferably through a shaft on which the truncated cone members are mounted. The phase separator 6 has an inlet which communicates with the flow path 3 at a position downstream of the heat exchange means 12 and as shown a conduit 25 effects the communication therebetween. The phase separator also has a discharge 26 which communicates with the flow path 3 via a conduit 27 and also the discharge 26 can be connected to other equipment for processing products separated in the phase separator 6. A pump 34 and valve 35 can be provided in the conduit 27 to assure adequate pressure for inducing flow of medium into the flow path 3 and the valve 35 is operable to control the flow rate, if any, of the medium into the flow path 3. The discharge 26 communicates with the flow path 3 at a point downstream of the point of communication of the inlet conduit 25 with the flow path 3; that is, the inlet is positioned between the medium discharge end 28 of the heat exchange means 12 and the point of communication of the conduit 27 with the tubular member 2.

Optionally, additional suitable heat exchangers 30 can be in heat transfer relation with the tubular member 2 at various positions along the tubular member 2.

Pump means is provided wherein a pump 31 communicates with the flow path 3 with an inlet conduit 32 to the pump 31 communicating with the flow path 3 at a position between the nozzle 5, which is positioned adjacent the upstream end 29 of the means 4, and the point of communication of the discharge 26 with the flow path 3. Pump outlet 33 is in communication with the nozzle 5 for discharge of pressurized medium therethrough. It is to be noted that the pump 31 is positioned exteriorly of the tubular member 2; however, it is also to be noted that same can be positioned within the flow path 3 and achieve the same results. As described above, the positions of the inlets and outlets for the pump 31 and the phase separator 6 are described in terms of flow along the tubular member 2 as opposed to an actual physical location.

As seen in FIG. 1, a plurality of pumps 31, means 4 and phase separators 6 can be provided along the length of the tubular member 2. Operation of the apparatus 1 is such that medium flows along the flow path 3 in a generally horizontal plane because the tubular member 2 is disposed in a generally horizontal plane whereas the phase separator 6 would be in a generally vertical plane wherein the discharge 26 would be at the bottom thereof as opposed to the way it is illustrated in FIG. 1. The axis of the phase separator would be generally vertical.

Figure 4:
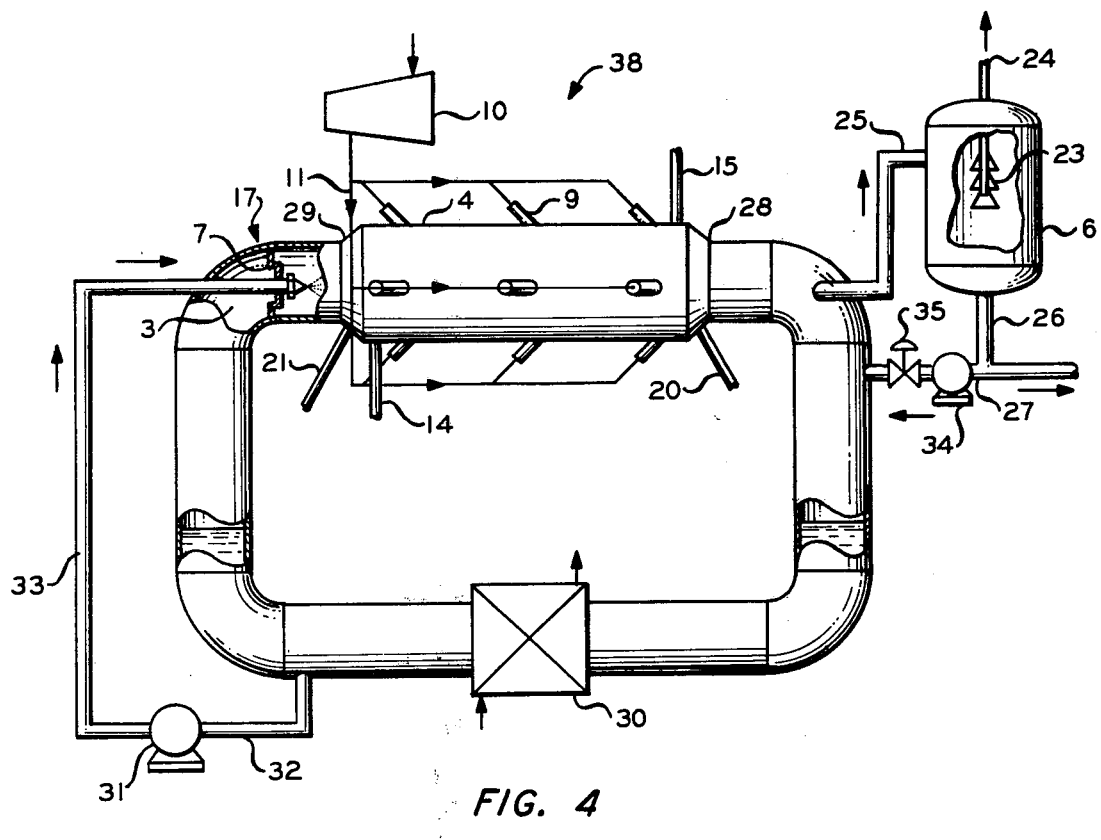
FIG. 4 is a somewhat schematic elevational view of a modified form of the fermentation apparatus.

FIG. 4 shows a modified form of the present invention wherein like numerals designate like or similar parts or structure. The reference numeral 38 denotes the modified form of apparatus and same has the means 4 phase separator means 6 and pump means 31 connected to a nozzle 5. The major difference between the forms of the invention shown in FIG. 1 and FIG. 4 is that the tubular member 2 in FIG. 4 is disposed in a generally vertical plane wherein the liquid phase separated by the phase separator can collect in the bottom thereof and can be returned to the fermentation zone of the tubular member 2 by discharge through the nozzle 5. The phase separator would again have its axis disposed generally vertically.

As best seen in FIG. 5 for both forms of the invention, another modification can be provided in that the medium can be injected into the flow path 3 in a generally tangential direction through one or more nozzles 5 wherein the mixing vanes 18 can be canted to effect a swirl motion of the medium within the flow path 3 and the fins 22 can also be canted to help effect swirl of the medium within the flow path 3. The air injectors 9 as seen in FIG. 5 are also directed generally tangentially to help effect swirl or vortex flow. Also, the conduit 27 communicates with the flow path 3 wherein the medium would be discharged in a generally tangential manner into the flow path 3.

Operation of the various forms of the invention described above are similar. A calculated example is provided below to illustrate operation of the above-described apparatus in which methanol is used as the carbon and energy source.

Typical operating parameters are:

| | |
|---|---|
| Cell yield: | 0.4 lb/lb methanol feed (estimated) |
| Oxygen required: | 2.09 lb. oxygen/lb cells produced |
| Cell concentration in fermenter broth: | 3.5 wt. percent |
| Cell concentration in liqd from foam separator: | 8 wt. percent |
| Reaction residence time: | 4 hours |
| Heat of fermentation: | 18,000 BTU per lb. of cells |
| Flow velocity of medium: | 10 ft. per sec. |
| Liquid/gas ratio: | Approx. 1 vol/vol |
| Air input pressure: | 35 psia |
| Fermentation temperature: | 40° C. (104° F.) |

EXAMPLE

For a fermenting apparatus having a capacity of approximately 7500 gallons, the following conditions would be typical, based on the operating parameters stated above:

| | | |
|---|---|---|
| 1. | Fermenter tubular member: | Two horizontal sections, as viewed in FIG. 1, 36" dia. × 28' long and two vertical sections, as viewed in FIG. 1, 30" dia. × 54' long joined into a rectangular loop by 4–30" elbows. |
| 2. | Methanol feed rate | 63 gallons per hour |
| 3. | Cell production rate: | 155 lb per hour |
| 4. | Gas dispersion: | 350 cfm air at 14.7 psia and 60° F. |
| 5. | Fluid medium circulation rate: | 22,000 gpm |
| 6. | Foam separator: | 3 ft. diameter by 6 ft. height of conventional type |
| 7. | Cooling water flow rate: | 2300 gpm at 20° F. temp. rise |
| 8. | Power required: | |
| | Air compressor | 50 hp |
| | Pumps | 100 hp |
| | Foam breaker | 20 hp |
| | Total | 170 hp |

It is to be understood that while there has been illustrated and described certain forms of this invention, it is not to be limited to the specific form or arrangement of parts herein described and shown except to the extent that such limitations are found in the claims.

What is claimed and desired to be secured by Letters Patent is:

1. A method of conducting fermentation in a loop flow type fermentation apparatus comprising a first conduit to a pressurizing means, a nozzle and a second conduit wherein said nozzle is positioned between said first conduit and said second conduit, said apparatus further having a flow path in and defined by a tubular member forming a substantially continuous loop, comprising the steps of
   (a) flowing medium along said flow path in and defined by said tubular member forming said substantially continuous loop;
   (b) removing a portion of said medium from said flow path via said first conduit;
   (c) pressurizing the thus removed medium in said pressurizing means;
   (d) atomizing the thus pressurized medium into small drops by discharging said pressurized medium into said flow path through said nozzle;
   (e) introducing assimilable oxygen adjacent said nozzle for mixing with the thus atomized medium and thereby forming a mixture;
   (f) removing heat from the resulting mixture as said mixture flows along at least a portion of said flow path;
   (g) mixing said mixture as it flows along at least a portion of said flow path;
   (h) withdrawing a portion of the thus mixed mixture from said flow path via said second conduit and separating the thus withdrawn portion into a gas phase and a liquid phase.

2. A method as set forth in claim 1 including:
   said medium is prevented from flowing through said flow path in loop flow except through said nozzle.

3. A method as set forth in claim 1 including:
   returning to said flow path at least a portion of the thus separated liquid phase of said withdrawn portion.

4. A method as set forth in claim 1 wherein:
   said assimilable oxygen is introduced into said flow path in a generally tangential direction.

5. A method as set forth in claim 1 wherein:
   said assimilable oxygen is introduced into said flow path in a generally radial direction.

6. A method as set forth in claim 1 wherein:
   said assimilable oxygen is introduced into said flow path in a generally downstream direction with respect to the nozzle.

7. A method as set forth in claim 1 wherein:
   said assimilable oxygen is introduced around said nozzle.

* * * * *